United States Patent [19]

Davies et al.

[11] Patent Number: 4,490,222
[45] Date of Patent: Dec. 25, 1984

[54] PREPARATION OF SELECTED EPOXIDES

[75] Inventors: Gwilym R. Davies, Cheshire; Alfred G. Williams, Berkshire, both of England

[73] Assignee: Imperial Chemical Industries PLC, London, England

[21] Appl. No.: 485,896

[22] Filed: Apr. 18, 1983

[30] Foreign Application Priority Data

Apr. 30, 1982 [GB] United Kingdom ................ 8212637

[51] Int. Cl.³ .............................................. C25B 3/02
[52] U.S. Cl. ....................................... 204/78; 204/128
[58] Field of Search ................................. 204/128, 78

[56] References Cited

U.S. PATENT DOCUMENTS

| 3,288,692 | 11/1966 | Leduc et al. | 204/80 |
| 3,394,059 | 7/1968 | Young | 204/78 |
| 3,497,431 | 2/1970 | Kronig et al. | 204/80 |
| 3,650,918 | 3/1972 | Johnson et al. | 204/80 |

FOREIGN PATENT DOCUMENTS

| 2237895 | 2/1975 | France | 204/78 |
| 2295035 | 7/1976 | France | 204/78 |
| 1467864 | 3/1977 | United Kingdom | 204/78 |
| 1476598 | 6/1977 | United Kingdom | 204/78 |

OTHER PUBLICATIONS

Simmrock, "Hydrocarbon Processing", vol. 57, pp. 105-113, (Nov. 1978).

Primary Examiner—R. L. Andrews
Attorney, Agent, or Firm—Cushman, Darby & Cushman

[57] ABSTRACT

A process for the production of epoxides of the formula (I):

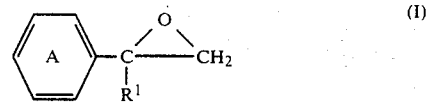

in which the benzene ring A is substituted with 1 to 3 halogen atoms, which are the same or different, and optionally carries other substituents, and $R^1$ is

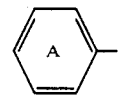

which is the same as or different from the other group

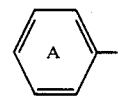

or $C_{1-6}$ alkyl, the process comprising electrolyzing the corresponding alkene of the formula (II):

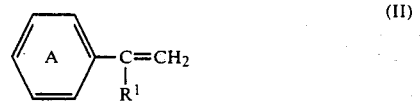

in a medium comprising a solvent for the alkene and an aqueous solution of a halogen salt, the solvent/water ratio by weight being greater than unity, the solvent being miscible with water at the solvent/water ratio used and being chemically inert to both the alkene and the free halogen produced from the halogen salt by the electrolysis.

The epoxides are useful in the synthesis of fungicidal compounds and certain of the epoxides are novel compounds.

10 Claims, No Drawings

PREPARATION OF SELECTED EPOXIDES

This invention relates to a process for the preparation of epoxides useful in the synthesis of fungicidal compounds, and to certain of the epoxides themselves.

For preparing terminal epoxides, there is substantial disclosure in the literature of direct epoxidation of terminal alkenes, with selectivity and in good yield, using a variety of oxidising agents. However, we have found that if we follow the known procedures with certain alkenes, we do not generally obtain the selectivity and good epoxide yields which might otherwise be expected from the prior art. For example, when attempting metal catalysed oxidation reactions of certain halogen substituted-phenyl alkenes by alkyl hydroperoxidation and reactions using hydrogen peroxide with benzonitrile as catalyst, we detected no epoxides in the product, sometimes despite conversion of the alkenes. Likewise, other known alkene epoxidising agents such as 2-hydroperoxy hexafluoropropanol give complete conversion of the alkene without any identifiable epoxides being present in the product, and even treatment with bromine and caustic produced only poor yields via the bromohydrin intermediate.

An electrochemical route via the bromohydrin, has also been described for a variety of alkenes ranging from ethylene to stilbene (e.g. in GB No. 1,467,864 and U.S. Pat. No. 3,288,692), in which the alkene is bubbled into an electrolyte consisting of an aqueous solution of an alkali metal (or sometimes alkaline earth metal) halide and electrolysed. To improve the solubility of the alkene in these essentially electrically conducting aqueous conditions, the addition of solvents such as dimethyl formamide has been proposed, although we are not aware of any reported experiment in which such solvents were used. However, attempts at direct epoxidation of our terminal halogen substituted-phenyl alkenes alkenes using the aqueous conditions exemplified in the prior art, even with small amounts of dimethyl formamide added, gave very poor results and appeared to indicate that this route, like others, was not effective for epoxidising our alkenes.

We have now found that by substantially altering the process conditions from those previously used, selective conversion of our alkenes to their corresponding epoxides can be achieved, with good yields of epoxide, by an electrochemical method.

According to the present invention there is provided a process for the production of epoxides of the formula (I):

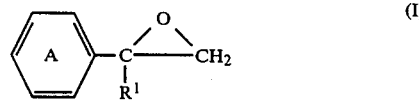

in which the benzene ring A is substituted with 1 to 3 halogen atoms, preferably chlorine or fluorine atoms, which are the same or different, and optionally carries other substituents, and $R^1$ is

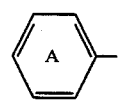

which is the same as or different from the other group

or $C_{1-6}$ alkyl, the process comprising electrolysing the corresponding alkene of the formula (II):

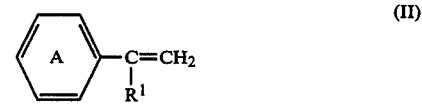

in a medium comprising a solvent for the alkene and an aqueous solution of a halogen salt, the solvent/water ratio by weight being greater than unity, the solvent being miscible with water at the solvent/water ratio used and being chemically inert to both the alkene and the free halogen produced from the halogen salt by the electrolysis.

Despite the reactions in the anodic and cathodic regions being ionic reactions involving water and/or hydroxide, we find we obtain optimum results when the water content is relatively small. Our preferred range of water contents is from 3 to 25% by volume of total medium. Within this range our best results to date have been obtained with a water content within the very narrow range of 5 to 10%, again expressed as percentage by volume of the total medium. Reducing the water content down to 3% by volume was found not to increase the cell voltage unduly. However the current is carried by the ions, and hence the minimum useful level of water will be determined largely by the solubility of the halide salt, although it can also be affected by the stochiometry of the olefin. However in the limit, for effective production of epoxide the medium may need at least 1 mol of water per mol of alkene as the water takes part in the reaction. This does give a theoretical water minimum of around 3% by volume, which is consistent with the fall off in efficiency which we have found in practice with water contents of less than 3% by volume. At high water levels, we have found that the addition of alkene may induce the medium to form two layers. This does not appear to affect the reaction, however, provided the water and solvent are miscible in the absence of alkene.

In addition to its inertness with respect to the other materials in the medium during electrolysis, we prefer our solvent for the alkene to have a high dielectric constant to reduce solution resistance, dielectric constants greater than 30 being particularly suitable. Preferred solvents include dimethyl formamide, acetonitrile, sulpholane, N-methyl pyrrolidone, dimethyl acetamide and dimethyl sulphoxide. Solvents having lower dielectric constants, such as diglyme and tertiary butanol for example (with dielectric constants of about 8 and 20 respectively), while being otherwise suitable at higher water concentrations within the range, do tend to produce higher cell voltages, especially at low water concentrations, and hence are generally less suitable.

An undesirable by-product of the reaction is the haloalkene and we find that the yield of this byproduct (at the expense of the epoxide yield) tends to increase with increasing free halogen concentration. The free halogen is produced at the anode during the electrolysis, and provides the halogen for the halohydrin reaction, and reactions (using bromine as the halogen, for example) are believed to be as follows

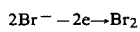

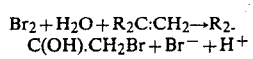

We find that by surpressing the free bromine by addition of a base at the start of the reaction, the formation of the by-product is likewise surpressed with corresponding increased yield (based on initial alkene) of the epoxide, this latter apparently being formed according to the cathodic reactions $$2H_2O + 2e^- \longrightarrow H_2 + 2OH^-$$

$$R_2C(OH){:}CH_2Br + OH^- \longrightarrow R_2C\overset{O}{\underset{\phantom{O}}{-\!\!-\!\!-}}CH_2 + Br^- + H_2O$$

Accordingly we prefer that the initial pH of the medium be greater than 7, and we prefer to achieve this by a process in which base is added to the medium until the colour of the free halogen just disappears. The base can be an alkali metal hydroxide, but we find that whereas reasonable results can be achieved with alkali metal hydroxides in laboratory scale experiments, particularly with the lower solvent/water ratios within the specified range, on larger scale preparations we find that sodium salts tend to precipitate out of solution. We find that this can be alleviated by using as base, ammonium hydroxide (which can be added as gaseous ammonia) or substituents thereof.

Similarly, although the halogen salts can be alkali metal halides in the manner of the aqueous electrochemical pocesses of the prior art (alkaline earth metal ions preferably being avoided), we prefer to use ammonium salts to avoid the precipitation of alkali metal salts referred to above. Thus to generalise for both the added base and the halide, we prefer that at least half and preferably all the cations other than hydronium ions present in the medium, be ammonium, substituted ammonium or a mixture thereof. Bulky tetralkyl ammonium ions such as the tetrabutyl ammonium ions, have the advantage of being generally more soluble in solvents for the alkene listed above, but under some conditions can result in side reactions at the cathode. Accordingly we prefer to compromise by using the unsubstituted ammonium ions.

Our preferred halogen salt is a bromide, as bromides are generally more soluble in our preferred solvents than the corresponding chlorides, and we find that this is advantageous in the present process by causing the generation of bromine from bromide ions to occur at lower electrode potentials. The cell voltage can also be reduced by increasing the concentration of bromide, e.g. as ammonium bromide, but this can apparently also lead to a side reaction giving the aldehyde isomer of the epoxide, and we prefer to restrict the halide concentration to the molar range 0.1–0.2M, adding further base to increase the total ion content of the medium.

The process of the invention is of particular value for the preparation of epoxides of the formula (III):

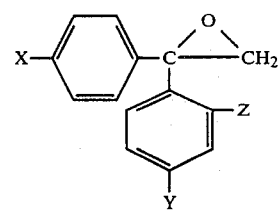

from the corresponding alkenes of the formula (IV):

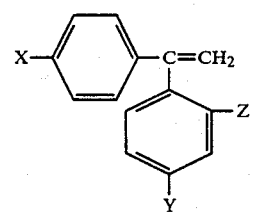

in which X and at least one of Y and Z are each independently fluorine or chlorine, Y or Z otherwise being halogen; and epoxides of the formula (V):

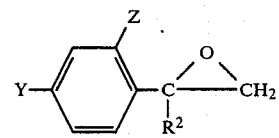

from the corresponding alkenes of the formula (VI):

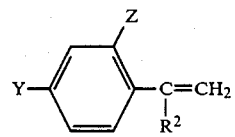

in which Y and Z have the meanings given above and $R^2$ is $C_{1-6}$ alkyl, preferably $C_{1-4}$ alkyl and especially n-butyl.

The epoxides of formula (I) above are useful intermediates in the synthesis of fungicidal compounds of formula (VII) below:

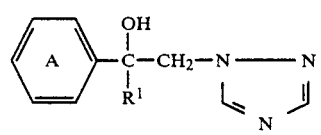

in which the benzene ring A and $R^1$ have the meanings previously defined, which are described in, for example, European Patent Specifications Nos. 15756 and 48548. The fungicidal compounds of the formula (VII) may be obtained by reacting the epoxide of the formula (I) with 1,2,4-triazole in the presence of an acid binding agent or with an alkali metal salt of the triazole, conveniently in a solvent such as dimethyl formamide.

Particularly useful epoxides are those of the formula (III) above which have the following substitution patterns for X, Y and Z:

| X | Y | Z |
|---|---|---|
| F | F | H |
| F | H | F |
| F | H | Cl |
| Cl | H | Cl |
| Cl | F | H |
| F | Cl | Cl |

Also mentioned are epoxides of the formula (V) above in which at least one of Y and Z is fluorine or chlorine, and especially both are chlorine, and $R^2$ is n-butyl.

The alkenes of formula (II) which are used as starting materials in the present process may be obtained by a Grignard reaction between methyl magnesium halide and a compound of the formula (VIII):

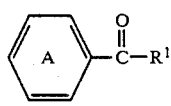  (VIII)

in which the benzene ring A and $R^1$ have the meanings previously defined and dehydrating the alcohol formed in the Grignard reaction.

The invention is illustrated by the following Examples in which experiments were carried out in an Eberson cell, a filter press cell or a beaker cell. The Eberson cell consisted essentially of a central anode surrounded by a coaxial cylindrical cathode. The anode was a carbon rod having an exposed length of 47 cm and a diameter of 4.7 cm. The cathode was formed of stainless steel and was separated from the anode by a 1 mm gap. The cell was mounted vertically with an inlet port at the lower end and an outlet port at the upper end. The filter press cells were of conventional construction with two rectangular electrodes separated by an inert spacer defining a path for the solution to flow between the electrodes. The beaker cell was simply a 50 ml beaker with a cathode wrapped around a central anode and circulation provided by a magnetic stirrer.

EXAMPLE 1

To 160 g of approximately 96% strength 2-chloro-4'-fluoro-1,1-diphenylethene (containing 153.6 g of the alkene, 0.66 moles) contained in a 1 liter volumetric flask, was added NaBr (5.1 g), 880 Ammonia (27.6 ml, containing 15.8 ml of $H_2O$) and water (35.7 ml). Dimethyl formamide was added up to 1 liter and the solution stirred until all the alkene had dissolved. This produced a solution containing NaBr (0.05M), $NH_3$ (0.5M), alkene (0.63M, measured by gas/liquid chromatography—glc) and water (5.1% by volume).

This solution was poured into a reservoir attached to the Eberson cell described above, and pumped through the cell at a rate of 8 liters/minute (this being a rate found suitable for this solution in this cell). After circulation was established, the power supply was switched on and 40 amps were passed through the cell at an initial 12 volts. During the reaction the voltage rose steadily but was reduced again after 125 minutes by the addition of further sodium bromide (5.1 g). As the solution circulated it was passed over a cold condenser and this maintained the temperature in the region 35°–40° C. throughout the reaction.

During the reaction the concentration of the starting alkene and the formation of products was monitored using glc. There was a 4% increase in solution density as water was used up, but the figures given below have been normalised to the original mass balance before calculation of yields and efficiencies. After 180 minutes of electrolysis, glc indicated that most of the starting alkene had reacted (98.9% conversion), and the solution was drained from the cell. Analysis of the medium after normalising to 100%, indicated a final composition as follows: starting alkene 0.007M, epoxide 0.566M, aldehyde 0.021M, and bromoalkene 0.037M. Current efficiencies, based on the total current passed are for loss of starting alkene 27.9%, epoxide formation 25.3%, aldehyde 0.9% and bromoalkene 1.7%. Product efficiencies based on loss of weight of starting alkene were epoxide 90.7%, aldehyde 3.4% and bromoalkene 5.9%.

The final solution contained a white solid (5 g), which settled out once cell circulation was stopped. This solid was filtered off, washed with ether, and dried. Elemental analysis gave C 14.7%; H 0.90%; N 0.34%; Na 33.2%; Br N.D.; and ash content 70.8%. This is consistent with the solid being mainly $NaHCO_3$ (calculated: C 14.3%; H 1.2%; Na 27.4%; ash 63.1%).

The products in the final solution were identified by glc comparison with standard samples, and by coupling the epoxide in solution with triazole to give an overall yield of the tertiary alcohol fungicide of 65% based on the starting alkene.

EXAMPLES 2–6

Effect of water concentration

The experimental details and results of a series of reactions at different water concentrations are summarised in Table 1. The general procedure described in Example 1 was followed, except that different alkenes and different cells were used in some experiments as indicated in the Table.

Example 3, using t-butanol as solvent, resulted in a relatively poor yield of the desired epoxide (50%), and the two other quoted co-products (aldehyde and bromoalkene) do not account for the remaining reacted alkene. In fact two other less volatile peaks were observed on glc trace, accounting for at least 20% of the starting alkene.

TABLE I

| | Effect of water concentration | | | | |
|---|---|---|---|---|---|
| Example | 2 | 3 | 4 | 5 | 6 |
| Experiment | 58 | 62 | 15 | 49 | D16 |
| Water vol % | 37[5] | 37 | 10 | 5 | 3.6 |
| Solvent | Diglyme | t-Butanol | DMF | DMF | DMF |
| Alkene; conc M | $A^3$; 0.016 (aq layer) = 1.36[1] | A; = 1.18[2] | $B^4$; 0.36 | B; 0.72 | B; 0.8 |
| Homo- or Heterogeneous | 2 phase | 3 phase | Homogeneous | Homogeneous | Homogeneous |
| Bromide, conc M | NaBr, 0.1 | NaBr, 0.1 | KBr, 0.05 | $NH_4Br$, 0.1 | $nBu_4NBr$ 0.1 |
| Hydroxide, conc M | NaOH, 0.1 | NaOH, 0.1 | KOH, 0.05 | $NH_3$ 0.5 | $nBu_4NOH$ 0.05 |
| Cell | Filter Press | Filter Press | Filter Press | Filter Press | Beaker Cell |
| Anode | Platinised Titanium | Plantinised Titanium | Plantinum | Plantinised Titanium | Carbon |

TABLE I-continued

| | Effect of water concentration | | | | |
|---|---|---|---|---|---|
| Example | 2 | 3 | 4 | 5 | 6 |
| Experiment | 58 | 62 | 15 | 49 | D16 |
| Cathode | Stainless Steel | Stainless Steel | Platinum | Stainless Steel | Steel |
| Electrode Area sq cm | 200 | 200 | 30 | 200 | 6.16 |
| Current Density mA/sq cm | 50 | 50 | 90 | 50 | 100 |
| Electrode gap mm | 3 | 3 | 10 | 1 | 10 |
| Pumping Rate 1/min | 4 | 4 | 1 | 1 | Magnetic stirrer |
| Temperature °C. | 26.5–28.5 | 27.5–31 | 25–30 | 20–23 | 25 |
| Alkene Conversion % | 15.7 | 71.5 | 96.7 | 92.9 | 97.6 |
| Alkene Current Eff % | 11.5 | 32.8 | 34.2 | 44.8 | 21.8 |
| Epoxide CE % | 8.9 | 16.5 | 30.9 | 37.9 | 20.2 |
| Epoxide Yield % | 77.6 | 50.2 | 90.3 | 84.6 | 92.5 |
| Aldehyde Yield % | 17.3 | 9.1 | 4.0 | 14.2 | 2.8 |
| Bromoalkene Yield % | 5.1 | 1.7 | 5.7 | 1.2 | 4.6 |
| Tertiary Alcohol Yield % (if coupled) | — | — | 47.1 | — | 45.7 |

[1] Most of the alkene remains as a lower layer, the amount of alkene used would give a 1.36 M solution if it was homogeneous.
[2] The mixture is not homogeneous, but the amount of alkene used would give a 1.18 M solution for a homogeneous system.
[3] Alkene A = 2,4'-difluor-1,1-diphenyl ethene
[4] Alkene B = 2-chloro-4'-fluoro-1,1-diphenyl ethene
[5] The solvent/water ratio by weight was 50/50.

EXAMPLES 6–10

Effect of bromide source

The experimental details and results of a series of reactions using various sources of bromide, in combination with a base, are given in Table 2.

It should be noticed that the epoxide yields from the two alkenes used are generally different for the same conditions, but the trends in yields are apparently in the same direction as conditions are varied.

TABLE 2

| | Effect of bromide source | | | | |
|---|---|---|---|---|---|
| Example | 6 | 7 | 8 | 9 | 10 |
| Experiment | D16 | 34 | 30 | 17 | 15 |
| Bromide, conc M | nBu₄NBr, 0.1 | NH₄Br, 0.1 | NH₄Br, 0.1 | NaBr, 0.05 | KBr, 0.05 |
| Hydroxide, conc M | nBu₄NOH 0.05 | NH₃, 0.5 | NH₃, 0.5 | NaOH, 0.05 | KOH, 0.05 |
| Water vol % | 3.6 | 5 | 5 | 5 | 10 |
| Solvent | DMF | DMF | DMF | DMF | DMF |
| Alkene; conc M | B, 0.8 | A, 0.66 | A, 1.51 | B, 0.47 | B, 0.36 |
| Cell | Beaker Cell | Eberson | Eberson | Filter Press | Filter Press |
| Anode | Carbon | Carbon | Carbon | Platinum | Platinum |
| Cathode | Steel | Stainless Steel | Stainless Steel | Platinum | Platinum |
| Electrode Area sq cm | 6.16 | 700 | 700 | 30 | 30 |
| Current Density mA/sq cm | 100 | 57 | 57 | 100 | 90 |
| Electrode Gap mm | 10 | 1 | 1 | 3 | 10 |
| Pumping Rate 1/min | Magnetic Stirrer | 8 | 8 | 1 | 1 |
| Temperature °C. | 25 | 30–40 | 25–30 | 25 | 25 |
| Alkene Conversion % | 97.6 | 99.4 | 100 | 99.4 | 96.7 |
| Alkene Current Eff % | 21.8 | 35.2 | 49.2 | 24.7 | 34.2 |
| Epoxide CE % | 20.2 | 30.2 | 40.5 | 22.6 | 30.9 |
| Epoxide Yield % | 92.5 | 85.2 | 82.4 | 91.5 | 90.3 |
| Aldehyde Yield % | 2.8 | 10.7 | 12.8 | 0 | 4.0 |
| Bromoalkene Yield % | 4.6 | 4.1 | 2.5 | 8.5 | 5.7 |
| Tertiary Alcohol Yield % (if coupled) | 45.7 | — | 58.0 | 50.9 | 47.1 |

EXAMPLES 11–13

Use of bromide without added base

The experimental details given in Table 3 summarise a series of 3 reactions carried out using sodium bromide as the bromide source with no base added. Although reasonable yields of epoxide are obtained, the experiments quoted produced relatively high yields of bromoalkene.

TABLE 3

| | Use of bromide without added base | | |
|---|---|---|---|
| Example | 11 | 12 | 13 |
| Experiment | 6 | 7 | 8 |
| Bromide; conc M | NaBr; 0.1 | NaBr; 0.3 | NaBr; 0.1 |
| Water, vol % | 10 | 10 | 10 |
| Solvent | DMF | DMF | DMF |
| Alkene; conc M | B; 0.48 | B; 0.49 | B; 0.48 |
| Cell | Filter Press | Filter Press | Filter Press |
| Anode | Platinum | RUO₂ on Titanium | Pt/Ir on Titanium |
| Cathode | Monel | Platinum | Platinum |
| Electrode Area sq cm | 30 | 30 | 30 |
| Current Density mA/sq cm | 50 | 50 | 50 |
| Electrode Gap mm | 10 | 10 | 10 |
| Pumping Rate 1/min | 1 | 1 | 1 |
| Temperature °C. | 20 | 34 | 44 |
| Alkene Conversion % | 53.6 | 27.6 | 46.8 |
| Alkene Current Eff % | 75.9 | 48.6 | 66.4 |
| Epoxide CE % | 65.5 | 32.2 | 51.5 |
| Epoxide Yield % | 86.3 | 66.2 | 77.6 |
| Aldehyde Yield % | 0 | 9.8 | 4.9 |
| Bromoalkene Yield % | 13.3 | 24.5 | 17.5 |

EXAMPLES 14 AND 15

Comparison of experiments with and without added base

Two identical experiments, apart from the presence of 0.1M nBu₄NOH in one case, are compared in Table 4. Using the more soluble tetra alkyl ammonium salts (rather than sodium salts for example) there is very little difference between the measured epoxide yields and current efficiencies. However the presence of 0.1M nBu₄NOH results in a reduced cell voltage and thus leads to power savings.

TABLE 4

Comparison of experiments with and without added base

| Example | 14 | 15 |
| --- | --- | --- |
| Experiment | 62 | 64 |
| Bromide; conc M | nBu₄NBr; 0.1 | nBu₄NBr; 0.1 |
| Hydroxide; conc M | nBu₄NOH; 0.1 | — |
| Initial Cell Voltage | 9.9 | 12.2 |
| Final Cell Voltage | 10.4 | 13.4 |
| Water, vol % | 5 | 5 |
| Solvent | DMF | DMF |
| Alkene; conc M | A; 1.39 | A; 1.34 |
| Cell | Filter press | Filter press |
| Anode | Platinised Titanium | Plantinised Titanium |
| Cathode | Stainless Steel | Stainless Steel |
| Electrode Area sq cm | 200 | 200 |
| Current Density mA/sq cm | 50 | 50 |
| Electrode Gap mm | 3 | 3 |
| Pumping Rate l/min | 1.8 | 1.8 |
| Temperature °C. | 27-31 | 28.5-32 |
| Alkene Conversion % | 45.7 | 46.2 |
| Alkene Current Eff % | 28.3 | 27.6 |
| Epoxide CE % | 24.8 | 23.5 |
| Epoxide Yield % | 87.4 | 86.8 |
| Aldehyde Yield % | 5.9 | 7.9 |
| Bromoalkene Yield % | 6.6 | 5.3 |

EXAMPLE 16

To 200 g of 2,4-dichloro-4'-fluoro-1,1-diphenylethene (0.75 mole) contained in a 1 liter volumetric flask was added NaBr (20 g), 880 Ammonia (50 ml, containing 32.5 ml H₂O) and water (50 ml). Dimethyl formamide was added up to 1 liter and the solution stirred until all the alkene had dissolved.

This produced a solution containing NaBr (0.485M), alkene (0.75M) and water (8.25% by volume).

This solution was poured into a reservoir attached to the Eberson cell described previously, and pumped through the cell at a rate of 8 liters/minute (this being a rate found suitable for this solution in this cell). After circulation was established the power supply was switched on and 40 amps were passed through the cell at an initial 5 volts, rising to 10 volts at the end of the reaction period. As the solution circulated it was passed over a cold condenser and this maintained the temperature in the region of 23°-28° C. throughout the reaction.

During the reaction the concentration of residual alkene and the formation of products were monitored using glc. After 270 minutes of electrolysis, 99% conversion of the alkene was achieved. The current efficiency, based on the total current passed, for loss of alkene was 22.3%.

The yield and quality of the epoxide were measured by coupling the epoxide with triazole to give an overall yield of the tertiary alcohol fungicide of 60% based on starting alkene.

EXAMPLE 17

To 101 g of approximately 92% strength 2,4'-difluoro-1,1-diphenylethene (containing 93 g of the alkene, 0.43 moles) contained in a 1 liter volumetric flask, was added NH₄Br (9.8 g), and 1M sodium hydroxide solution (50 ml=2 g NaOH). Dimethyl formamide was added to 1 liter and the solution stirred to dissolve the alkene.

This produced a solution containing NH₄Br (0.1M), NaOH (0.05M), alkene (0.43M) and water (5% by volume).

This solution was poured into a reservoir attached to the Eberson cell described previously, and pumped through the cell at a rate of 8 liters/minute (this being a rate found suitable for this solution in this cell). After circulation was established the power supply was switched on and 40 amps were passed through the cell at an initial 7 volts, rising to 12 volts at the end of the reaction period. As the solution circulated it was passed over a cold condenser and this maintained the temperature in the region of 23°-28° C. throughout the reaction.

During the reaction the concentration of residual alkene and formation of products were monitored using glc. After 90 minutes of electrolysis, 99% conversion of the alkene was achieved. The current efficiency based on the total current passed, for loss of alkene was 38.4%.

The yield and quality of the epoxide were measured by coupling the epoxide in solution with triazole to give an overall yield of the tertiary alcohol fungicide of 67.5% based on the starting alkene.

EXAMPLE 18

To 101 g of 2,4-dichloro-1-phenyl-1-n-butylethene (0.44 moles) contained in a 1 liter beaker was added NH₄Br (9.8 g), 880 Ammonia (25 ml, containing 16.25 ml of H₂O) and water (25 ml). Dimethyl formamide (700 ml) was added and the solution stirred until all the alkene had dissolved. This produced a solution containing NH₄Br (0.14M), NH₃ (0.73M), alkene (0.44M) and water (5.9% by volume).

The solution was poured into a reservoir attached to the Eberson cell described previously and pumped through the cell at a rate of 8 liters/minute (this being a rate found suitable for this solution in this cell). After circulation was established, the power supply was switched on and 40 amps were passed through the cell at an initial 9 volts, rising to 16 volts at the end of the reaction period. As the solution circulated it was passed over a cold condenser and this maintained the temperature in the region of 23°-27° C. throughout the reaction.

During the reaction the quality and rate of conversion were monitored using glc. After 120 minutes electrolysis 98% conversion of the alkene was achieved.

The yield and quality were measured by coupling the epoxide in solution with triazole to give an overall yield of the tertiary alcohol fungicide of 87.1% based on the starting alkene.

NMR Analysis

A sample of the product in DMF (10.1 g) was extracted with carbon tetrachloride. The extracts were washed first with dilute hydrochloric acid to remove DMF and then with water, and the sample evaporated to give 2.46 g of a CCl₄ solution.

Analysis by NMR was consistent with the product being the epoxide of the formula

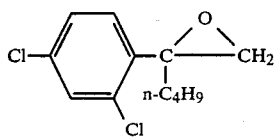

Analysis (1) $\delta$0.7–2.4 (9H) aliphatic complex (n-butyl group)
(2) Two doublets: $\delta$61, 2.90: J 5.4 HZ (2 protons)
(3) $\delta$7.0–7.5 (3 protons).

What is claimed is:

1. A process for the production of epoxides of the formula (I):

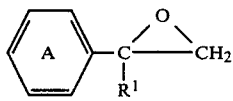

in which the benzene ring A is substituted with 1 to 3 halogen atoms, which are the same or different, and optionally carries other substituents, and $R^1$ is

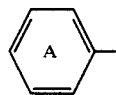

which is the same as or different from the other group

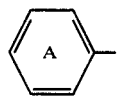

or $C_{1-6}$ alkyl, the process comprising electrolysing the corresponding alkene of the formula (II):

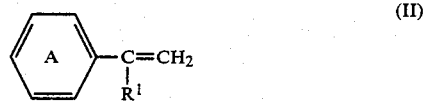

in a medium comprising a solvent for the alkene and an aqueous solution of a halogen salt, the solvent/water ratio by weight being greater than unity, the solvent being miscible with water at the solvent/water ratio used and being chemically inert to both the alkene and the free halogen produced from the halogen salt by the electrolysis.

2. A process according to claim 1 in which the water content of the medium is from 3 to 25% by volume of the total medium.

3. A process according to claim 1 in which the water content of the medium is from 5 to 10% by volume of the total medium.

4. A process according to claim 1 in which there is present in the medium at least 1 mol of water per mol of alkene.

5. A process according to claim 1 in which the solvent has a dielectric constant greater than 30.

6. A process according to claim 1 in which the solvent is selected from dimethyl formamide, acetonitrile, sulpholane, N-methyl pyrrolidone, dimethyl acetamide and dimethyl sulphoxide.

7. A process according to claim 1 in which the initial pH of the medium is greater than 7.

8. A process according to claim 1 in which at least half of the cations other than hydronium ions present in the medium are ammonium, substituted ammonium or a mixture thereof.

9. A process according to claim 1 in which the halogen salt is a bromide.

10. A process according to claim 1 in which the halide concentration is in the molar range 0.1 to 0.2M.

* * * * *